United States Patent [19]

Ko et al.

[11] Patent Number: 4,850,372
[45] Date of Patent: Jul. 25, 1989

[54] ELECTROMAGNETIC NON-INVASIVE MEASUREMENT AND MONITORING SYSTEM FOR OSTEOPOROSIS

[75] Inventors: Harvey W. Ko, Columbia; Joseph P. Skura, Ellicott City, both of Md.

[73] Assignee: The Johns Hopkins University, Baltimore, Md.

[21] Appl. No.: 89,193

[22] Filed: Aug. 25, 1987

[51] Int. Cl.⁴ .............................................. A61B 5/05
[52] U.S. Cl. ..................................... 128/734; 128/653
[58] Field of Search ................ 128/804, 653, 734; 324/308, 321

[56] References Cited

U.S. PATENT DOCUMENTS

| | | | |
|---|---|---|---|
| 4,510,450 | 4/1985 | Brown | 324/308 |
| 4,520,826 | 6/1985 | Sevastyanov et al. | 128/804 |
| 4,635,643 | 1/1987 | Brown | 128/653 |
| 4,642,558 | 2/1987 | Batchman et al. | 128/653 |
| 4,688,580 | 8/1987 | Ko et al. | 128/734 |

Primary Examiner—Francis J. Jaworski
Assistant Examiner—George Manuel
Attorney, Agent, or Firm—Robert E. Archibald; Howard W. Califano

[57] ABSTRACT

A method for noninvasively sensing bone mass loss associated with osteoporosis is disclosed. The method uses an electromagnetic field to measure impedance (or conductivity) changes in the bone. A decrease in conductivity is indicative of osteoporosis.

7 Claims, 3 Drawing Sheets

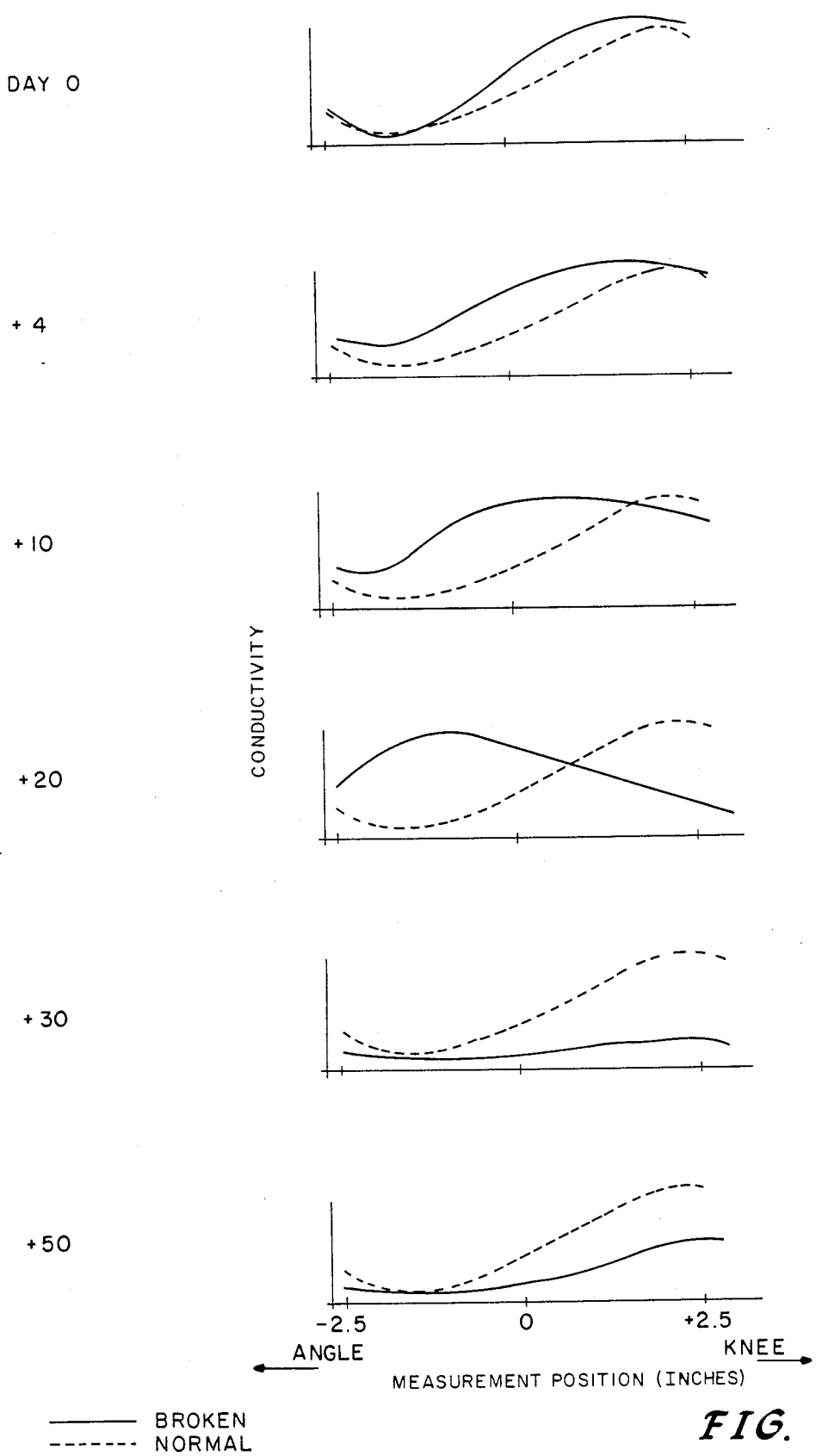

ELECTROMAGNETIC NON-INVASIVE MEASUREMENT AND MONITORING SYSTEM FOR OSTEOPOROSIS

STATEMENT OF GOVERNMENTAL INTEREST

The Government has rights in this invention pursuant to Contract No. N00039-87-C-5301 awarded by the Department of the Navy.

BACKGROUND OF THE INVENTION

1. Field of the Invention

The invention relates to a method and apparatus for measuring and monitoring osteoporosis in an animal or human patient. More particularly, the invention uses an electromagnetic field to non-invasively measure impedance changes in a bone as a monitor of osteoporosis.

2. Description of the Prior Art

Osteoporosis is a condition characterized by a loss of bone mass. It can result because of a variety of causes that include chronically restricted calcium intake, hyperparathyroidism, hypersteroidism, immobilization, and weightlessness. Lay people also associate osteoporosis with the aging process. Various prior art x-ray techniques are of some assistance in detecting a loss of bone mass. However, no safe, inexpensive, non-invasive technique is taught by the prior art to regularly monitor osteoporosis.

The present invention uses an electromagnetic field to non-invasively measure impedance changes in a bone as a monitor of osteoporosis. As will be discussed in detail subsequently in this application, Applicants have related the impedance change in a bone with bone mass loss associated with osteoporosis. U.S. Pat. No. 3,735,245 entitled "Method and Apparatus for Measuring Fat Content in Animal Tissue Either in Vivo or in Slaughtered and Prepared Form", invented by Wesley H. Harker, teaches that the fat content in meat can be determined by measuring the impedance difference between fat and meat tissue. The Harker apparatus determines gross impedance change and does not provide adequate spatial resolution for the present use. U.S. Pat. No. 4,240,445 teaches the use of an electromagnetic field responsive to the dielectric impedance of water to detect the presence of water in a patient's lungs. However, such an apparatus does not detect the conductivity variations required in the present invention. U.S. Pat. No. 3,789,834 relates to measurement of body impedance by using a transmitter and receiver and computing transmitted wave impedance from the electrical or magnetic field generated. However, the antenna pickup would receive extraneous noise rendering it inappropriate for the present use. None of the above-cited references contemplate measuring the loss of bone mass associated with osteoporosis by measuring the impedance of the bone and none of the references teach an apparatus capable of specifically detecting such impedance.

SUMMARY OF THE INVENTION

The present inventors realized through experimentation that impedance (or conductivity) changes in a bone could be related to the loss of bone mass associated with osteoporosis. They discovered that bone conductivity, measured by a remote electromagnetic means, is decreased for patients with osteoporosis.

The present invention uses a non-invasive electromagnetic field and detects a change in mutual inductance of a sensor coil. The basic sensor utilizes a thin or narrow magnetic field coil winding which spatially concentrates the magnetic field and detects the impedance (or conductivity) of the bone. As a limb is passed within the proximity of the spatially discrete coil detector, the mutual inductance of the coil is detected and produces a change in the resonant amplitude and resonant frequency of the detection oscillator. The invented apparatus is capable of detecting small variations in impedance changes and quantitatively measuring such changes. The oscillator detector in combination with the magnetic coil is specifically designed to be sensitive to small impedance changes and to reduce polarization effects and background noise which could render such monitoring impossible. The detecting apparatus was described in the following co-pending patent applications, also assigned to The John Hopkins University, for use in monitoring bone healing and monitoring physiological changes in the brain: "Electromagnetic Bone Healing Sensor Using a Multi-coil Sensor Array", invented by Harvey W. Ko et al and filed of even date herewith; "Electromagnetic Bone Healing Sensor", invented by Harvey W. Ko et al U.S. Pat. No. 4,688,580; and, "Non-invasive Electromagnetic Technique for Monitoring Physiological Changes in the Brain", invented by Harvey W. Ko U.S. Pat. No. 4,640,149.

A first novel feature of the invention is the method of measuring and monitoring osteoporosis by measuring impedance (or conductivity) changes in a patient's bone.

A second novel feature of the invention is the use of a coil winding and oscillating detector to non-invasively detect impedance (or conductivity) in a patient's bone by detecting changes in the coils mutual inductance.

BRIEF DESCRIPTION OF THE DRAWINGS

FIG. 4 is a series of graphs illustrating bone mass loss detected in association with the fracture healing process.

DETAILED DESCRIPTION OF THE EMBODIMENT

Figure 1:
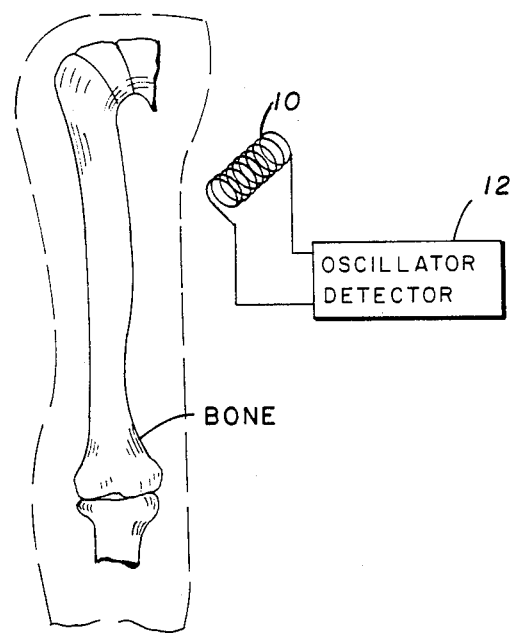
FIG. 1 is a block diagrammatic illustration of the present invention showing a coil detector used to detect impedance (or conductivity) changes in the patient's bone.

The present invention is an electromagnetic sensor for osteoporosis based on Applicants' discovery that the electrical impedances (or conductivity) of a bone will change with the loss of bone mass associated with osteoporosis. FIG. 1 is a schematic representation of the sensor as taught by the present invention. The basic sensor includes a magnetic field coil 10, and an oscillator/detector 12. The apparatus uses the same principle as some metal detectors which are used at the airport.

As the conducting material passes within the proximity of the coil detector, the mutual inductance of the coil in the electronic circuit changes the frequency of oscillation of the detector circuit. The amount of oscillation is proportional to the value of the electrical conductivity passing through the detector coil. The magnetic field of the coil creates an electric field. The electric field creates induced eddy currents within the conducting bone material. These induced eddy currents re-radiate a magnetic signal, which is detected by the detector coil. The amount of magnetic field which is re-radiated is proportional to the amount of eddy current which in induced. The amount of eddy current which is induced in proportional to the electrical conductivity of the bone. In operation the coil 10 would be scanned across the bone as measurements are taken (or alternatively, a single measurement can be taken at a designated site). The readings could be compared to "normal readings"—a decrease in conductivity below the "normal" would indicate bone mass loss. Alternatively, the conductivity measurements taken over time for a particular patient could be compared to monitor bone mass loss associated with osteoporosis.

Figure 2:
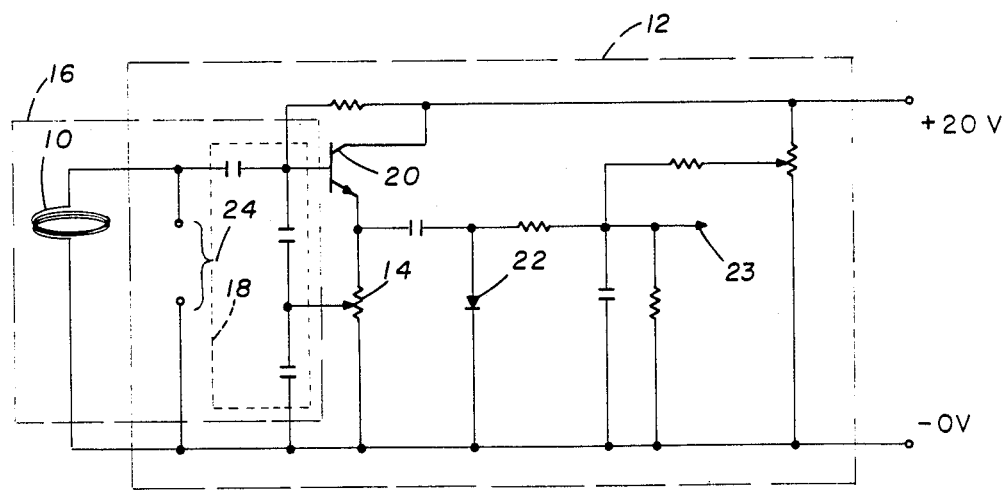
FIG. 2 is a schematic diagram of a typical detection circuit used with the present invention.

FIG. 2 is a schematic drawing of one possible circuit configuration for oscillator detector 12. Electronically, the circuit represents a marginally stable Colpitts oscillator whose frequency of oscillation is determined by the tank circuit. Although a Hartley-type oscillator, or similar, would work equally well. The potentiometer tap 14 helps to find the proper circuit resistance external to the tank circuit 16 resistance needed for stable oscillation. The tank circuit 16 includes coil 10 and capacitors 18. The transistor 20 with negative feedback provides stable voltage gain. A DC output 23 is extracted from the demodulator diode 22 which reflects the change in oscillator amplitude. The frequency is measured directly off coil 10 at output 24. When a bone is placed through coil 10, eddy currents are induced by the time changing magnetic field generated by the coil. The eddy currents in turn produced a secondary, though slight, magnetic field whose associated flux is coupled back to the coil. This produces a change in the coil impedance which changes the resonant amplitude, measured at output 23, and the resonant frequency, measured at output 24, of tank circuit 16. The coil inductances are in the millihenry (mH) range so that resonant frequencies in the hundreds of kHz to several MHz are obtained. In this frequency range, the impedance changes are dominated by conductivity properties and not polarization effects caused by the relative permittivity of the media.

Figure 3:
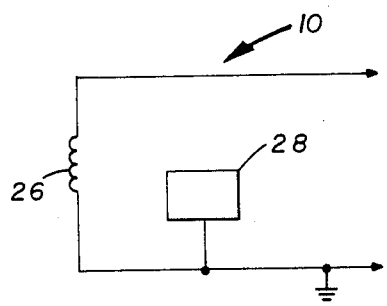
FIG. 3 is a schematic diagram of a typical coil sensor used with the present invention.

FIG. 3 is a sensor coil 10 used with the present invention, although other sensor coils could be used. The coil 10 includes a ten-turn, air-core winding of magnetic wire 26 and a thin sheet of copper used as a Faraday shield 28.

FIG. 4 is a series of graphs generally showing the conductivity profile along legs taken during a bone fracture healing process. The measurements were compiled from actual dog trials. Each graph in FIG. 4 is a plot of conductivity (calculated from the measurements) versus measurement position. The results are shown at measurement positions that extend from 2.5 inches below the fracture (toward the ankle) to 2.5 inches above the fracture (toward the knee). The measurement position "0" is directly over the fracture. The trend results from the fractured leg are given by the solid line. The results from the normal leg are given by the dotted line. Six graphs are given stylizing the results obtained on the day of surgery (day 0) and aproximately 4, 10, 20, 30, 50 days after surgery. Each measurement day, the case is removed, data are taken on the skin, and then the cast is replaced. Note in FIG. 4 that at measurement positions well above the fracture (about 2.5 inches) the fractured bone conductivity at Day 10 and beyond falls much below the normal conductivity value. Examination of x-rays show that there is practically no muscle atrophy but, in fact, lesser bone density. The loss in conductivity in these measurements is attributed to osteoporosis.

Figure 5:
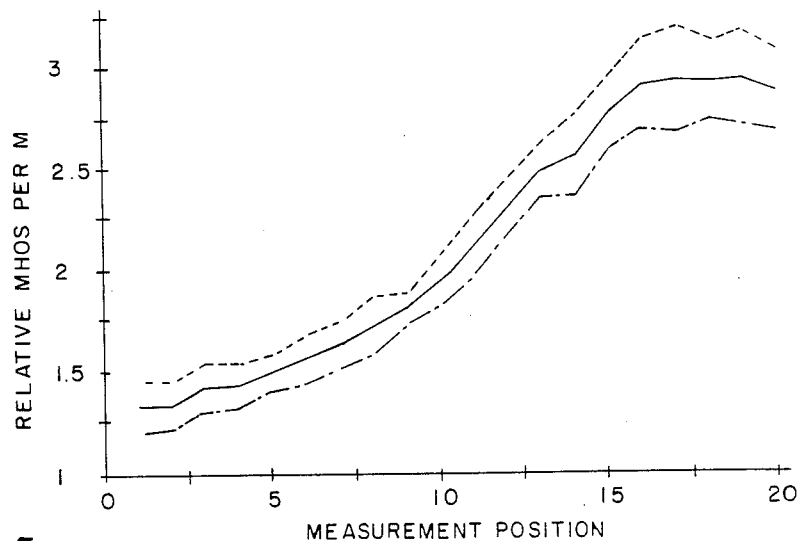
FIG. 5 is a graph showing the normal conductivity profile for a normal hind leg of a relatively young dog, taken using the present invention.
Figure 6:
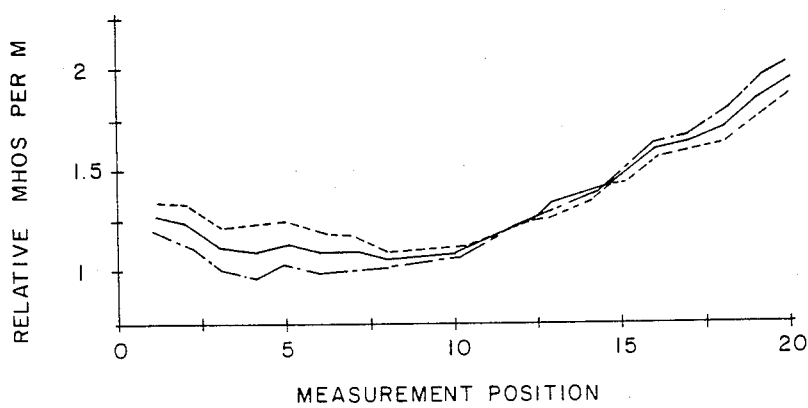
FIG. 6 is a graph showing the normal conductivity profile for a normal hind leg of a relatively old dog having osteoporosis, taken using the present invention.

FIGS. 5 and 6 are conductivity profiles for the hind leg of two dogs; however, FIG. 5 shows data taken from a dog about 18 months old and FIG. 6 shows data taken from a dog about 10 to 12 years old with believed osteoporosis. When FIGS. 5 and 6 are compared, we see not only dramatic "flattening out" of the conductivity plotted against positions, but also that the conductivity levels measured for the older dog is much lower than the younder dog. This drop in conductivity is indicative of osteoporosis.

Other embodiments of this invention have been contemplated by the inventors for measurement and monitoring of osteoporosis. For example, detector coils could be packaged in a plug or puck that is placed against the forehead; or coils could be implanted under the skin or muscle with a tiny transmitter to help monitor continuously.

Obviously many modifications and variations of the present invention are possible in light of the above teachings. It is, therefore, to be understood that within the scope of the appended claims the invention may be practiced otherwise than is specifically described.

What is claimed is:

1. A method for monitoring osteoporosis, comprising the steps of:
noninvasively measuring the impedance an intact non-fractured bone and other biological material in a region of a bone at plurality of different times; said measuring step further comprising,
generating an oscillating near field magnetic flux that is spatially concentrated in said region of the bone thereby producing eddy currents primarily in bone and secondarily in other biological matter located in said region of the bone, such eddy currents inducing a secondary magnetic emission which varies in response primarily to the impedance of said bone and secondarily to other biological matter located in said region of said bone,
detecting said induced secondary magnetic emission and displaying an informational signal indicating the local impedance in said region of the bone; and,
comparing said impedance measurements to monitor osteoporosis of the bone wherein a decrease in conductivity in said region of the bone is indicative of osteoporosis.

2. The method of claim 1, wherein noninvasively measuring impedance for each of said plurality of times comprises the following steps:
producing an oscillating magnetic field that is spatially concentrated in said region of the bone using a coil means, whereby eddy currents induced in bone and other biological matter will induce a secondary magnetic emission which alters the mutual inductance of said coil means in accordance with the impedance of bone and other biological matter is said region; and, detecting a change in said mutual inductance of said coil means, wherein an increase in mutual inductance indicates an increase in impedance and a decrease in mutual inductance indicate a decrease in impedance.

3. The method of claim 2, wherein said producing step comprises the step of exciting said coil means at a resonant frequency using an oscillator means, wherein said detecting step comprises the step of detecting changes in resonance caused by variations in said mutual inductance, wherein a higher resonant amplitude will indicate a higher impedance region.

4. A method of detecting osteoporosis, comprising the steps of:

noninvasively measuring the impedance of an intact non-fractured bone and other biological matter at a plurality of localized regions along a bone; said measuring step for each of said plurality of localized regions further comprises, generating a spatially concentrated oscillating near field magnetic flux at each particular region of said bone to induce eddy currents in bone and other biological matter within said region, such eddy currents inducing a secondary magnetic emission which varies in response to the impedance of bone and other biological matter within said region, detecting said induced secondary magnetic emission and displaying an informational signal indicating the impedance detected at said region; and, comparing said impedance measurements with a normal conductivity profile to detect osteoporosis, wherein a drop-in conductivity below the normal conductivity profile is indicative of osteoporosis.

5. The method of claim 4, wherein noninvasively measuring impedance for each of said plurality of regions comprises the following steps:

producing an oscillating magnetic field that is spatially concentrated in a localized region along said bone using a coil means, whereby eddy currents induce a secondary magnetic emission which alters the mutual inductance of said coil means in accordance with the impedance of bone and other biological matter in said region; and, detecting a change in the mutual inductance of said coil means, wherein an increase in mutual inductance indicates an increase in impedance and a decrease in mutual inductance indicates a decrease in impedance.

6. The method of claim 5, wherein said producing steps comprise the step of exciting said coil means at a resonant frequency using an oscillator means, wherein said detecting step comprises the step of detecting changes in the resonance caused by variations in said mutual inductance.

7. A method for monitoring osteoporosis, comprising the steps of:

generating an oscillating near field magnetic flux that is spatially concentrated in an intact non-fractured region of a patient's bone thereby producing eddy currents primarily in bone, such eddy currents inducing a secondary magnetic emission which varies in response primarily to the impedance of said bone; and, detecting said induced secondary magnetic emission and displaying an informational signal indicating local impedance in said region of the bone, wherein a decrease in impedance is indicative of a decrease in bone density and of osteoporosis.

* * * * *